US010132144B2

(12) United States Patent
Lawson et al.

(10) Patent No.: US 10,132,144 B2
(45) Date of Patent: Nov. 20, 2018

(54) GEOCHEMICAL METHODS FOR MONITORING AND EVALUATING MICROBIAL ENHANCED RECOVERY OPERATIONS

(71) Applicants: Michael Lawson, Spring, TX (US); Amelia C. Robinson, Houston, TX (US); Daniel A. Stolper, Berkeley, CA (US)

(72) Inventors: Michael Lawson, Spring, TX (US); Amelia C. Robinson, Houston, TX (US); Daniel A. Stolper, Berkeley, CA (US)

(73) Assignee: ExxonMobil Upstream Research Company, Spring, TX (US)

( * ) Notice: Subject to any disclaimer, the term of this patent is extended or adjusted under 35 U.S.C. 154(b) by 0 days.

(21) Appl. No.: 15/668,395

(22) Filed: Aug. 3, 2017

(65) Prior Publication Data
US 2018/0066504 A1  Mar. 8, 2018

Related U.S. Application Data

(60) Provisional application No. 62/382,921, filed on Sep. 2, 2016.

(51) Int. Cl.
*E21B 43/16* (2006.01)
*C09K 8/582* (2006.01)
(Continued)

(52) U.S. Cl.
CPC ............. *E21B 43/16* (2013.01); *C09K 8/582* (2013.01); *C09K 8/90* (2013.01); *E21B 43/25* (2013.01);
(Continued)

(58) Field of Classification Search
CPC .. C09K 8/58; C09K 8/582; C09K 8/90; E21B 43/16
See application file for complete search history.

(56) References Cited

U.S. PATENT DOCUMENTS 4,833,915 A    5/1989   Radd et al.
4,905,761 A    3/1990   Bryant
(Continued)

FOREIGN PATENT DOCUMENTS

CN         102154453 A      8/2011
WO    WO 2002/059351 A2    8/2002
(Continued)

OTHER PUBLICATIONS

Chung et al. (1988) "Origin of gaseous hydrocarbons in subsurface environments: theoretical considerations of carbon isotope distribution", *Chemical Geology*, vol. 71, pp. 97-103.
(Continued)

*Primary Examiner* — Zakiya W Bates
*Assistant Examiner* — Crystal J Miller
(74) *Attorney, Agent, or Firm* — Exxonmobil Upstream Research Company—Law Department (57) ABSTRACT

Described herein are methods and techniques that utilize molecular geochemistry and isotopic signatures to monitor microbial enhanced gas and oil recovery operations. The methods and techniques utilize multiply substituted isotopologue signatures, clumped isotope signatures, and/or position-specific isotope signatures of one or more byproducts of the microbial stimulation techniques to determine the effectiveness of a microbial stimulation technique.

18 Claims, 2 Drawing Sheets

(51) Int. Cl.

| | | |
|---|---|---|
| *C09K 8/90* | (2006.01) | |
| *E21B 43/25* | (2006.01) | |
| *G01N 33/28* | (2006.01) | |
| *G01V 9/00* | (2006.01) | |
| *C12P 1/00* | (2006.01) | |
| *C12P 39/00* | (2006.01) | |

(52) U.S. Cl.
CPC ......... *G01N 33/2823* (2013.01); *G01V 9/007* (2013.01); *C12P 1/00* (2013.01); *C12P 39/00* (2013.01)

(56) References Cited

U.S. PATENT DOCUMENTS

| | | |
|---|---|---|
| 5,388,456 A | 2/1995 | Kettel |
| 5,439,800 A | 8/1995 | Thompson |
| 6,613,520 B2 | 9/2003 | Ashby |
| 6,645,769 B2 | 11/2003 | Tayebi et al. |
| 7,124,030 B2 | 10/2006 | Ellis |
| 7,174,254 B2 | 2/2007 | Ellis |
| 7,210,342 B1 | 5/2007 | Sterner et al. |
| 7,249,009 B2 | 7/2007 | Fermworn et al. |
| 7,297,661 B2 | 11/2007 | Beyer et al. |
| 7,337,660 B2 | 3/2008 | Ibrahim et al. |
| 7,395,691 B2 | 7/2008 | Sterner et al. |
| 7,529,626 B1 | 5/2009 | Ellis |
| 7,571,644 B2 | 8/2009 | Ibrahim et al. |
| 7,762,131 B2 | 7/2010 | Ibrahim et al. |
| 7,809,538 B2 | 10/2010 | Thomas |
| 8,071,295 B2 | 12/2011 | Ashby |
| 8,316,933 B2 | 11/2012 | Kohr |
| 8,316,934 B2 | 11/2012 | Pietrobon |
| 8,355,872 B2 | 1/2013 | Rowan |
| 8,476,016 B2 | 7/2013 | Ashby |
| 8,505,375 B2 | 8/2013 | Smalley |
| RE44,728 E | 1/2014 | Pope et al. |
| 8,695,703 B2 | 4/2014 | Dinariev et al. |
| 8,714,246 B2 | 5/2014 | Pop et al. |
| 8,760,657 B2 | 6/2014 | Pope et al. |
| 8,950,251 B2 | 2/2015 | Valentine |
| 9,068,107 B2* | 6/2015 | Larter .................. C09K 8/582 |
| 9,146,225 B2 | 9/2015 | Pottorf et al. |
| 9,594,879 B2 | 3/2017 | Eiler |
| 9,612,231 B2 | 4/2017 | Pottorf et al. |
| 9,670,395 B2 | 6/2017 | McDaniel |
| 2006/0154306 A1 | 7/2006 | Kotlar et al. |
| 2007/0251146 A1* | 11/2007 | Larter .................. C09K 8/582 48/127.5 |
| 2008/0040086 A1 | 2/2008 | Betancourt et al. |
| 2008/0147326 A1 | 6/2008 | Ellis |
| 2009/0071239 A1 | 3/2009 | Rojas et al. |
| 2010/0015612 A1 | 1/2010 | Pelham et al. |
| 2010/0086180 A1 | 4/2010 | Wallace |
| 2010/0257004 A1 | 10/2010 | Perlmutter et al. |
| 2010/0279290 A1 | 11/2010 | Sleat et al. |
| 2011/0250582 A1 | 10/2011 | Gates et al. |
| 2011/0308790 A1 | 12/2011 | Strapoc et al. |
| 2012/0134749 A1 | 5/2012 | Darrah |
| 2012/0158306 A1 | 6/2012 | Busche et al. |
| 2013/0091925 A1* | 4/2013 | Darrah .................. G01V 5/06 73/23.35 |
| 2013/0103337 A1 | 4/2013 | Eiler |
| 2013/0116126 A1 | 5/2013 | Ashby et al. |
| 2014/0011692 A1 | 1/2014 | Ashby |
| 2014/0138528 A1 | 5/2014 | Pope et al. |
| 2014/0162274 A1 | 6/2014 | Kunin et al. |
| 2014/0182840 A1 | 7/2014 | Sheehy et al. |
| 2014/0202684 A1 | 7/2014 | Danait et al. |
| 2014/0250999 A1 | 9/2014 | Lawson et al. |
| 2014/0288853 A1 | 9/2014 | Dreyfus et al. |
| 2014/0303895 A1 | 10/2014 | Dreyfus et al. |
| 2014/0378319 A1 | 12/2014 | Regberg et al. |
| 2015/0038348 A1 | 2/2015 | Ashby et al. |
| 2015/0127313 A1 | 5/2015 | Lawson et al. |
| 2015/0240633 A1* | 8/2015 | Akkurt .................. E21B 49/088 175/50 |
| 2015/0284810 A1 | 10/2015 | Knight et al. |
| 2015/0291992 A1 | 10/2015 | Al-Moniee et al. |
| 2016/0018558 A1* | 1/2016 | Bond .................. G01V 8/02 250/255 |
| 2016/0084045 A1 | 3/2016 | Lawson et al. |
| 2016/0084080 A1 | 3/2016 | Lawson et al. |
| 2016/0084081 A1 | 3/2016 | Lawson et al. |
| 2016/0084817 A1 | 3/2016 | Lawson et al. |
| 2016/0222781 A1 | 8/2016 | Lawson et al. |
| 2016/0222782 A1* | 8/2016 | Lawson .............. G01N 33/241 |
| 2016/0258922 A1* | 9/2016 | Formolo ............... E21B 49/00 |
| 2016/0272962 A1 | 9/2016 | Kohr |
| 2016/0341038 A1* | 11/2016 | AbuAli ................. G01N 1/2294 |

FOREIGN PATENT DOCUMENTS

| | | |
|---|---|---|
| WO | WO 2007/008932 | 1/2007 |
| WO | WO 2010/109173 A1 | 9/2010 |
| WO | WO 2013/148442 A1 | 10/2013 |

OTHER PUBLICATIONS

Lazar C.S. et al. (2011) "Distribution of Anaerobic Methane-Oxidizing and Sulfate-Reducing Communiteis in the G11 Nyegga Pockmark, Norwegian Sea", Antoine van Leeuwenhoek, vol. 100, pp. 639-653.
Mangelsdorf et al. (2011) "Microbial Lipid Markers Within and Adjacent to Challenger Mound in the Belgica Carbonate Mound Province, Porcupine Basin, Offshore Ireland (IODP Expedition 307)", *Marine Geology*, vol. 282, pp. 91-101.
Ozgul (2002), "Geochemical Assessment of Gaseous Hydrocarbons: Mixing of Bacterial and Thermogenic Methane in the Deep Subsurface Petroleum System, Gulf of Mexico Continental Slope", *Thesis in partial fulfillment of the requirements for the degree of Master of Science at Texas A&M University*, pp. 1-167.
Prinzhofer et al. (2003), "Gas Isotopes Tracing: An Important Tool for Hydrocarbons Exploration", *Oil & Gas Science and Technology—Rev. Ifp.*, vol. 58, No. 2, pp. 299-311.
Berner, U. et al., "Maturity Related Mixing Model for Methane, Ethane and Propane, Based on Carbon Isotopes," *Advances in Organic Geochemistry* 13(1-3), (1987), pp. 67-72.
Bigeleisen, J. et al., "Calculation of Equilibrium Constants for Isotopic Exchange Reactions," *J. of Chemical Physics*, 15(5), (May 1947), pp. 261-267.
Bloino, J. et al., "General Perturbative Approach for Spectroscopy, Thermodynamics and Kinetics: Methodological Background and Benchmark Studies," *J. of Chemical Theory and Computation* 8, (2012), pp. 1015-1036.
Burnham, A.K. et al., "A Chemical Kinetic Model of Vitrinite Maturation and Reflectance," *Geochimica et Cosmochimica Acta* 53, (1989), pp. 2649-2657.
Bryant, R.S. et al., "Review of Microbial Technology for Improving Oil Recovery," *SPE Reservoir Engineering* 4, (1989), pp. 151-154.
Chung, H.M., et al., "Use of Stable Carbon Isotope Compositions of Pyrolytically Derived Methane as Maturity Indices for Carbonaceous Materials," *Geochimica et Cosmochimica Actam* 43, (1979), pp. 1979-1988.
Glasstone, S. et al., "The Theory of Rate Processes," *J. of Chemical Education*, (May 1942), p. 249.
Hassanzadeh, G. et al., "Petroleum System Analysis Using Geochemical Studies, Isotope and 1D Basin Modeling in Hendijan Oil Field, SW Iran," Int'l. Petroleum Conf., 14797, (2011), pp. 1-11.
Hohl, D. et al., "DCO Energy, Environment and Climate Directorate White Paper," DCO Energy, Environment and Climate Workshop, (Jul. 21-22, 2010), Houston, TX, pp. 1-34.
James, A.T., "Correlation of Reservoired Gases Using the Carbon Isotopic Compositions of Wet Gas Components," *American Ass. of Petroleum Geologists Bulletin* 74(9), (Sep. 1990), pp. 1441-1458.
Li, G. et al., "Microbial Abundance and Community Composition Influence Production Performance in a Low-Temperature Petroleum Reservoir," *Environmental Science & Technology* 48, (2014), pp. 5336-5344.

(56) References Cited

OTHER PUBLICATIONS

Liu, Q. et al., "On the Proper Use of the Bigeleisen-Mayer Equation and Corrections to it in the Calculation of Isotopic Fractionation Equilibrium Constants," *Geochimica et Cosmochimica Acta* 74, (2010), pp. 6965-6983.
Reeves, E.P. et al., "Hydrogen Isotope Exchange Between n-Alkanes and Water Under Hydrothermal Conditions," *Geochimica et Cosmochimica Acta* 77, (2012), pp. 582-599.
Richet, P. et al., "A Review of Hydrogen, Carbon, Nitrogen, Oxygen, Sulphur, and Chlorine Stable Isotope Fractionation Among Gaseous Molecules," *Ann. Rev. Earth Planet. Sci.* 5, (1977), pp. 65-110.
Rustad, J.R. et al., "Calculation of Boron-Isotope Fractionation Between $B(OH)_3(aq)$ and $BG(OH)_4^-(aq)$," *Geochimica et Cosmochimica Acta* 74, (2010), pp. 2843-2850.
Sandrea, I. et al., "Global Oil Reserves—Recovery Factors Leave Vast Target for EOR Technologies," *Oil & Gas Journal* 105, (Nov. 5, 2007), pp. 1-8.
Stahl, W.J. et al., "Carbon and Nitrogen Isotopes in Hydrocarbon Research and Exploration," *Chemical Geology* 20, (1977), pp. 121-149.
Stolper, D.A., "New Insights into the Formation and Modification of Carbonate-Bearing Minerals and Methane-Gas in Geological Systems Using Multiply Substituted Isotopologues," Thesis, California Institute of Technology, (2014), Pasadena, CA, pp. 1-160.
Stolper, D.A., "New Insights into the Formation and Modification of Carbonate-Bearing Minerals and Methane-Gas in Geological Systems Using Multiply Substituted Isotopologues," Thesis, California Institute of Technology, (2014), Pasadena, CA, pp. 161-305.
Stolper, D.A. et al., "Formation Temperatures of Thermogenic and Biogenic Methane," *Science* 344(6191), (Jun. 27, 2014), pp. 1500-1503.
Stolper, D.A. et al., "Distinguishing and Understanding Thermogenic and Biogenic Sources of Methane Using Multiply Substituted Isotopologues," *Geochimica et Cosmochimica Acta* 161, (2015), pp. 219-247.
Stolper, D.A. et al., "Combined C-D and D-D Clumping in Methane: Methods and Preliminary Results," *Geochimica et Cosmochimica Acta* 126, (2014), pp. 169-191.
Torgersen, T. et al., "Air-Xe Enrichments in Elk Hills Oil Field Gases: Role of Water in Migration and Storage," *Earth and Planetary Science Letters* 167, (1999), 239-253.
Truhlar, D.G. et al., "Simple Perturbation Theory Estimates of Equilibrium Constants from Force Fields," *J. Chem. Phys* 94(1), (Jan. 1, 1991), pp. 357-359.
Urey, H.C. et al., "Some Thermodynamic Properites of the $H^1H^2$, $H^1H^2$Molecules and Compounds Containing the $H^2$ Atom," *J. of Chemical Physics* 1, (Feb. 1933), pp. 137-143.
Van Hamme, J.D. et al., "Recent Advances in Petroleum Microbiology," *Microbiology and Molecular Biolology Review*, (Dec. 2003), pp. 503-549.
Vidler, M. et al., "Accurate Partition Function and Thermodynamic Data for Water," *J. of Chemical Physics* 113(21), (Dec. 1, 2000), pp. 9766-9771.
Wang, D.T. et al., "Nonequilibrium Clumped Isotope Signals in Microbial Methane," *Science* 348, pp. 428-431.
Wang, Y. et al., "Equilibrium $^2H/^1H$ Fractionations in Organic Molecules: I. Experimental Calibration of AB Initio Calculations," *Geochimica et Cosmochimica Acta* 73, (2009), pp. 7060-7075.
Webb, M.A. et al., "Position-Specific and Clumped Stable Isotope Studies: Comparison of the Urey and Path-Integral Approaches for Carbon Dioxide, Nitrous Oxide, Methane, and Propane," *J. of Physical Chemistry* 118, (2014), pp. 467-474.
Whiticar, M.J., "Stable Isotope Geochemistry of Coals, Humic Kerogens and Related Natural Gases," *Int'l. J. of Coal Geology* 32, (1996), pp. 191-215.

\* cited by examiner

GEOCHEMICAL METHODS FOR MONITORING AND EVALUATING MICROBIAL ENHANCED RECOVERY OPERATIONS

CROSS-REFERENCE TO RELATED APPLICATIONS

This application claims the benefit of U.S. Provisional Patent Application No. 62/382,921 filed Sep. 2, 2016, the disclosure of which is incorporated herein by reference.

FIELD OF THE INVENTION

Described herein are geochemical methods for monitoring and evaluating microbial enhanced recovery operations. In particular, described herein are methods for utilizing isotopic signatures, such as multiply substituted isotopologue signatures, clumped isotope signatures, and/or position-specific isotope signatures, to monitor and evaluate microbial enhanced gas and oil recovery operations.

BACKGROUND

Thermogenic hydrocarbons are generated in the subsurface from source rocks rich in organic matter. Following initial deposition, source rocks are buried and subjected to increasing temperature and pressure with increasing burial. Thermogenic hydrocarbons are then generated when the source rocks reach temperatures sufficient for the thermal conversion of organic material to kerogen and then to free liquid and/or gaseous hydrocarbon phases in a process called source rock maturation. Upon generation, the hydrocarbons may subsequently be expulsed from the soured rock and migrated in the subsurface to reservoir rocks (such as sandstones or limestones) that have sufficient porosity, structure, and an adequate seal that make them capable of trapping the hydrocarbon phase(s), allowing hydrocarbons to accumulate.

In contrast to thermogenic hydrocarbons which are generated during source rock maturation processes, biogenic hydrocarbons are generated as byproducts from microbial utilization of buried organic matter in the subsurface. The generation of biogenic hydrocarbons usually occurs early during sediment burial (e.g., primary biogenic gas generation), but can also occur during the degradation of thermogenic hydrocarbons, for example as a byproduct of microbial consumption of thermogenic hydrocarbons (e.g., secondary biogenic gas generation).

Conventional pressure depletion methods that are used to produce oil from subsurface accumulations typically result in only modest recovery factors. Often, approximately 60-80% of the oil in the subsurface remains inaccessible when such conventional pressure depletion production ends. As such, enhanced recovery methods, such as microbial enhanced oil recovery ("MEOR") techniques, are then used to try to access the residual oil to extend the life of the production field.

Similar challenges exist when producing biogenic gas fields that are present within coal seams or are sorbed to coal (i.e., coalbed methane). In such systems, biogenic gas is generated by the microbial degradation of the coal. However, over time the biogenic gas generation can decrease and the recovery factor can decrease. Similar to MEOR techniques, stimulation of the microbial populations in these coal systems can be undertaken to regenerate the microbial coalbed methane production to form microbial enhanced coalbed methane ("MECoM") and extend the production life of these types of assets.

MEOR and MECoM techniques typically involve either the external stimulation of in situ indigenous microbial communities or the introduction of exogenous microbial communities (e.g., microbial populations that are introduced to the subsurface through water/fluid injection into the subsurface). The use of microbial stimulation techniques can improve the properties of the crude oil in the formation; modify the wettability in the reservoir (e.g., the microorganisms can mediate changes in the wettability of oil droplets by growing on the droplet and changing the surface of the oil to a less hydrophobic surface); generate biosurfactants that can reduce interfacial tension; make the hydrocarbons more mobile in the subsurface (e.g., the microorganisms can produce lower molecular weight hydrocarbons by enzymatically cleaving larger hydrocarbons into smaller molecules, thereby reducing the crude oil's viscosity); alter the permeability of the formation (e.g., the microorganisms can produce low molecular weight organic acids from the biodegradation of hydrocarbons which can cause rock dissolution); increase formation pressure (e.g., the microorganisms can generate gases, such as carbon dioxide and nitrogen, that can affect the formation pressure); and/or increase the generation of biogenic gas in the formation.

While microbial stimulation techniques can be very useful, it can be difficult to accurately monitor their performance. That is, it can be difficult to obtain an accurate in situ sample of the microbial community to test and evaluate their performance. Further it can be difficult to predict which microbial stimulation techniques will perform the best and how different microbial communities will react and perform under the harsh environmental conditions deep in the subsurface, as it is difficult to replicate such conditions in a laboratory environment.

The environmental conditions (e.g., temperature, pressure, formation water salinity, reservoir lithology, etc.) of reservoir formations and coalbed systems can vary significantly. The structure of microbial communities (e.g., the type of microorganisms that are present in the community and their relative proportion of the total microbial population) are very sensitive to the environmental conditions as different microbial species have different tolerances for temperature, salinity, and nutrient supplies. For example, microbial communities that exist in shallow reservoirs with fresh formation water are likely different from those that prevail at deeper, warmer reservoirs with higher salinity formation water.

Further, in MEOR and MECoM techniques that involve the introduction of nutrients to the formation to stimulate indigenous microorganisms, the process of stimulating the indigenous microbes can be unpredictable. For example, the growth of the microbial community can produce beneficial effects by, for example, dislodging oil entrapped within the formation. However, alternatively, the grown of the microbial community can lead to increased consumption of light oils (e.g., short-chain alkanes) which can make the oil more viscous and, thus, lower the recovery factor.

Thus, there remains a need for methods and techniques to evaluate the efficiency and efficacy of microbial stimulation operations. In particular, there remains a need for methods and techniques for monitoring and evaluating the relative performance of different stimulation operations, for determining whether appropriate stimulation treatments are being employed for a given environment, and for determining whether an optimized frequency of treatments is being utilized.

Background references may include US Patent Application Publication Nos. US 2014/0250999 A1, and US 2014/0288853 A1; PCT Publications WO 2007/008932 A2, WO 2013/071187 A1, WO 2013/071189 A1, WO 2016/043980 A1, WO 2016/043981 A1, WO 2016/043982 A1, WO 2016/126396 A1, and WO 2016/126397 A1; and Bryant et al. (1989) "Review of Microbial Technology for Improving Oil Recovery", *SPE Reservoir Engineering*, Vol. 4, pp. 151-154; and Van Hamme et al. (2003) "Recent Advances in Petroleum Microbiology", *Microbiology and Molecular Biology Reviews*, Vol. 67, No. 4, pp. 503-549; and Sandrea et al. (2007) "Global Oil Reserves—Recovery Factors Leave Vast Target for EOR Technologies", *Oil & Gas Journal*, Vol. 105, pp. 44-47; and D. Hohl et al. (2010) "Energy, Environment and Climate Directorate White Paper", *DCO Energy, Environment, and Climate Workshop*, pp. 1-38; and G. Hassanzadeh et al. (2011) "Petroleum System Analysis Using Geochemical Studies, Isotope and 1D Basin Modeling in Hendijan Oil Field, SW Iran", *International Petroleum Technology Conference*, 14797, pp. 1-11; and Li et al. (2014) "Microbial Abundance and Community Composition Influence Production Performance in a Low-Temperature Petroleum Reservoir" *Environmental Science & Technology*, Vol. 48, pp. 5336-5344; and D. A. Stopler (2014) "New Insights Into the Formation and Modification of Carbonate-Bearing Minerals and Methane Gas in Geological Systems Using Multiply Substituted Isotopologues", California Institute of Technology Thesis, pp. 1-305; and Stopler et al. (2014) "Formation temperatures of thermogenic and biogenic methane", *Science*, Vol. 344, pp. 1500-1503; and Stopler et al. (2015) "Distinguishing and understanding thermogenic and biogenic sources of methane using multiply substituted isotopologues", *Geochimica et Cosmochimica Acta*, Vol. 161, pp. 219-247; and Wang et al. (2015) "Nonequilibrium clumped isotope signals in microbial methane", *Science*, Vol. 348, pp. 428-431.

SUMMARY

The methods and techniques described herein are directed to methods of producing hydrocarbons. The methods may generally comprise obtaining one or more samples from a well in a region of interest; analyzing the one or more samples to determine a baseline isotopic signature, where the baseline isotopic signature comprises one or more of multiply substituted isotopologues signatures, clumped isotope signatures, and position-specific isotope signatures; performing a microbial stimulation operation on the region of interest; obtaining one or more post-stimulation samples from the well; analyzing the post-stimulation to determine an induced isotopic signature, where the induced isotopic signature comprises one or more of multiply substituted isotopologues signatures, clumped isotope signatures, and position-specific isotope signatures; comparing the baseline isotopic signature and the induced isotopic signature; and determining whether the type of hydrocarbons (e.g., thermogenic hydrocarbons, biogenic hydrocarbons, or induced biogenic hydrocarbons) being produced by the well has changed.

These and other features, aspects, and advantages of the present disclosure will become better understood with regard to the following description and appended claims.

DETAILED DESCRIPTION OF THE DISCLOSURE

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention can be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

Exemplary methods described herein may be better appreciated with reference to flow diagrams. While for purposes of simplicity of explanation, the illustrated methodologies may be shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement various embodiments of an example methodology. Blocks may be combined or separated into multiple components. Furthermore, additional and/or alternative methodologies can employ additional blocks not shown herein. While the figures illustrate various actions occurring serially, it is to be appreciated that various actions could occur in series, substantially in parallel, and/or at substantially different points in time.

Various terms as used herein are defined below. To the extent a term used in a claim is not defined below, it should be given the broadest possible definition persons in the pertinent art have given that term as reflected in at least one printed publication or issued patent.

As used herein, the term "basin modeling" refers generally to any method or analysis which provides a representation of the history of a sedimentary basin or other subsurface section of interest and/or an estimate of timing of any component of a hydrocarbon system. For example, a basin model may be used to model, but is not limited to, a burial history, time a specific subsurface location or layer reached a certain temperature or maturity, time for how long a location was in a certain temperature range, timing of expulsion, timing of migration, and/or timing of accumulation. Generally a basin model is based on and/or constrained by measured or derived data representing present day conditions (e.g., stratigraphy, current bottom hole temperature, heat flow) or a condition in the past (e.g., water depth) on which a model of the past history of the area of interest is based. The calculations used to form the basin model may be performed using a processor or other computer system.

As used herein, the term "biosurfactants" refers to amphiphilic compounds produced on or by living surfaces, mostly microbial cell surfaces, or excreted extracellularly and contain hydrophobic and hydrophilic moieties that reduce surface tension and interfacial tensions between individual molecules at the surface and interface, respectively. The biosurfactants referred to herein are produced by the microorganisms in a reservoir or coalbed formation, and may be of use in emulsification and de-emulsification of crude oils through reduction of interfacial tension, and thereby aid in reducing the viscosity of the crude oil. Exemplary biosurfactants may include peptides, fatty acids, phospholipids, glycolipids, lipopepties, etc. Exemplary biosurfactants may have one of the following structures: mycolic acid, glycolipids, polysaccharide-lipid complex, lipoprotein or lipopeptide, phospholipid, or the microbial cell surface itself. Biosurfactants that may be of particular use in the present application may include, but not be limited to, emulsan, alasan, surfactin, rhamnolipid, lichenysen, glycolipids, viscosin, trehaloselipids, sophorolipids, peptidolipid, and mixtures thereof.

As used herein, the term "biopolymer" refers to a polymer produced by a microorganism. In general, exemplary biopolymers may include polysaccharides, polyesters, polyamides, etc. Particular biopolymers that may be of use in the present application may include, but not be limited to, xanthan, pullulan, levan, curdlan, dextran, sleroglucan, alginate, and mixtures thereof. The biopolymers referred to herein may be of particular use in modifying the injectivity profile and viscosity of crude oils and other formation fluids.

As used herein, "community composition" refers to the composition of organisms in the system. That is, the community composition is an indication of the types or organisms (e.g., bacteria vs. archaea, or species x vs. species y) that live or exist in the system.

As used herein, "community structure" refers to the abundance of each type of organism in the system. In particular, the community structure is an indication of the relative abundance of the different types of organisms in the system. For example, the community structure may indicate that the system comprises 10% bacteria and 90% archaea. In some embodiments, the community structure may look at only a subset of the organisms within the system and provide an indication of the relative abundance of certain species within the system as compared to other species within the system. For example, the community structure may indicate that the system comprises 25% species x, 40% species y, 30% species z, and 5% of unclassified species.

As used herein, "exemplary" means serving as an example, instance, or illustration. Any embodiment described herein as exemplary is not to be construed as preferred or advantageous over other embodiments.

As used herein, the term "fingerprint" or "geochemical fingerprint" refers to a collection of signatures or geochemical signatures that are associated with a particular region of interest.

As used herein, "hydrocarbons" are generally defined as molecules formed primarily of carbon and hydrogen atoms such as oil and natural gas. Hydrocarbons may also include other elements or compounds, such as, but not limited to, halogens, metallic elements, nitrogen, oxygen, sulfur, hydrogen sulfide ($H_2S$), and carbon dioxide ($CO_2$). Hydrocarbons may be produced from hydrocarbon reservoirs through wells penetrating a hydrocarbon containing formation. Hydrocarbons derived from a hydrocarbon reservoir may include, but are not limited to, petroleum, kerogen, bitumen, pyrobitumen, asphaltenes, tars, oils, natural gas, or combinations thereof.

As used herein, "hydrocarbon production" or "producing hydrocarbons" refers to any activity associated with extracting hydrocarbons from a well or other opening. Hydrocarbon production normally refers to any activity conducted in or on the well after the well is completed. Accordingly, hydrocarbon production or extraction includes not only primary hydrocarbon extraction but also secondary or tertiary production techniques, such as injection of gas or liquid for increasing drive pressure, mobilizing the hydrocarbon or treating by, for example chemical or hydraulic fracturing the wellbore to promote increased flow, well servicing, well logging, and other well and wellbore treatments.

As used herein, the term "isotope" refers to one of two or more atoms with the same atomic number but with different numbers of neutrons. Hydrocarbon molecules generally contain both carbon and hydrogen atoms and may contain a variety of isotopes. For example, each carbon atom in a hydrocarbon molecule can be present as one of two stable isotopes: $^{12}C$, which has 6 protons and 6 neutrons, and/or $^{13}C$, which has 6 protons and 7 neutrons. Similarly, each hydrogen atom in a hydrocarbon molecule can be present as one of two stable isotopes: H, which contains 1 proton and no neutrons, and/or deuterium (D), which has 1 proton and 1 neutron. As another example, helium can be present as one of two stable isotopes: $^3He$, which has 2 protons and 1 neutron, and/or $^4He$, which has 2 protons and 2 neutrons.

As used herein, the term "isotopologues" refers generally to molecules that have the same chemical composition, but have a different isotopic signature. For example, methane contains one atom of carbon and four atoms of hydrogen. Thus, each atom in the methane structure can contain one of the two stable isotopes of that atom, and as such there are ten possible isotopologues of methane.

As used herein, the term "multiply substituted isotopologues" refers generally to an isotopologue that contains at least two rare isotopes in its structure. For example, a multiply substituted methane isotopologue may contain one $^{13}C$ atom and one D atom, or at least two D atoms and no $^{13}C$ atom.

As used herein, the term "clumped isotopologue" refers generally to an isotopologue that contains at least two rare isotopes that share a common chemical bond in its structure. For example, a clumped isotopologue of methane contains one $^{13}C$ atom that shares a chemical bond with at least one D atom.

As used herein, the term "position specific isotope signature" refers generally to a compound that has multiple chemically or structurally distinct positions for a rare isotope to reside. For example, a position specific isotope signature in propane could refer to the position of the $^{13}C$ atom, which can be positioned either at the center of the compound or one of the end positions. Likewise, a position specific effect in propane could refer to the position of a D atom, which could be attached either to the central carbon or to one (or more) of the end position carbons.

A "microbe" is any microorganism that is of the domain Bacteria, Eukarya, or Archaea. Microbes include bacteria, fungi, nematodes, protazoans, archaebacteria, algae, dinoflagellates, molds, bacteriophages, *mycoplasma*, viruses, and viroids.

As used herein, the term "region of interest" refers to an interval, compartment, or reservoir where hydrocarbons, non-hydrocarbon gases, and/or water may reside. Likewise, "regions of interest" may refer to multiple intervals, compartments, or reservoirs where hydrocarbons, non-hydrocarbon gases, and/or water may reside.

As used herein, the term "inter-regional" or "inter-compartment" refers to comparisons of multiple geochemical fingerprints from multiple regions of interest including, but not limited to, compartments, intervals, or reservoirs. Deviations in "inter-regional" fingerprints may be derived from different proportions of individual regions or interest contributing to a combined flow stream during production or may be derived from multiple compartments that are connected in the subsurface that produce a fingerprint consistent with multiple inputs.

As used herein, the term "intra-regional" or "intra-compartment" refers to comparisons of multiple geochemical fingerprints derived from one region of interest including but not limited to compartments, intervals, or reservoirs. Deviations in "intra-regional" fingerprints may be derived from changes in the properties of one region of interest such that the fluids produced or processes occurring within one region of interest.

As used herein, the term "organic acid" refers generally to an organic compound with acidic properties. The organic acids referred to herein are produced by the microorganisms in a reservoir or coalbed formation, and may be of use in increasing the permeability of a formation as well as increasing emulsification. Organic acids that may be of particular interest in the present application may include, but are not limited to, acetic acids, butyric acid, and propionic acid.

As used herein, the term "stochastic distribution" refers generally to a system where the stable isotopes in a given population of molecules are distributed randomly among all possible isotopologues of a given species. The stochastic distribution is the reference frame from which deviations are measured and is used to provide a baseline to identify anomalies that may be associated with secondary isotope exchange processes.

As used herein, the term "signatures" refers to the relative abundances, concentrations, and/or ratios of various elements, isotopes, and/or isotopologues of a given species. For example, a signature may be derived from the clumped isotopes within a sample.

As used herein, the term "thermogenic" refers to hydrocarbons generated from kerogen that is currently/has in the past been subjected to high temperature and pressure.

Described herein are methods and techniques that utilize molecular geochemistry and isotopic signatures to monitor microbial enhanced gas and oil recovery operations. For example, the methods and techniques may monitor the multiply substituted isotopologue signatures, clumped isotope signatures, and/or position-specific isotope signatures of one or more byproducts of microbial stimulation techniques. Exemplary byproducts that may be monitored include, but are not limited to hydrocarbons (e.g., methane), biosurfactants, biopolymers, organic acids, and combinations thereof. For example, comparisons can be made between baseline isotopic signatures before stimulation and induced isotopic signatures that occur after stimulation. The methods can be utilized to determine which microbial communities perform better under a given set of environmental conditions and/or which nutrient supplies give the best recovery factors. Further, the methods can also be utilized to inform the frequency at which re-stimulation is necessary to maintain a constant flow of hydrocarbons at a given well location.

Bulk isotopic signatures (e.g., abundance or concentration of $\delta^{13}C$ and/or $\delta D$ in a sample) can typically be used to identify methane formed naturally in the deep subsurface, such as at depths greater than 500 meters, and to distinguish between methane formed from thermogenic sources and methane formed from biogenic sources. However, the bulk isotopic signatures of methane formed from biological processes in a laboratory or in subsurface environments that are oversupplied with nutrients (e.g., swamps or ponds) are often not distinguishable from that of biogenic gases that are formed in the deep subsurface.

Microbial stimulation of the deep subsurface to improve oil quality and/or assist in enhanced oil recovery operations results in the generation of biogenic gases. This "induced" biogenic gas is generated at faster rate (as compared to the "naturally" produced biogenic gases) as the system is now oversupplied with nutrients (similar to swamps and ponds at the surface). As such, the bulk isotopic signature of "induced" biogenic methane cannot be distinguished from "naturally" occurring biogenic methane. However, as described herein the multiply substituted isotopologue signatures, clumped isotope signatures, and/or position-specific isotope signatures can be used to distinguish between the "naturally" occurring biogenic gas and the "induced" biogenic gas. That is, natural subsurface biogenic and thermogenic gases have multiply substituted isotopologue signatures, clumped isotope signatures, and/or position-specific isotope signatures that are at internal isotopic equilibrium and which can be used to provide information about the temperature at which the gas was generated. Microbial gases that are generated by providing an oversupply of nutrients to artificially stimulate rapid grown of the microbial community are characterized by a kinetic isotopic effect (KIE) that is not at equilibrium, and thus do not correlate to the temperature at which the gas was formed.

Given the differences in the multiply substituted isotopologue signatures, clumped isotope signatures, and/or position-specific isotope signatures from indigenous thermogenic and biogenic hydrocarbons that are present in either trapped, unrecovered oil or as methane not produced from coals and the signatures of the induced biogenic gas, one can monitor the evolution and deviation in the signatures pre- and post-stimulation. The change in the gas signature can then be used to quantify the amount of induced hydrocarbons produced post-stimulation. This can then be used to compare differences in stimulation strategies (e.g., introduction of different microbial communities and/or different nutrient supplies). Also, because gas moves quicker than oil in the subsurface, monitoring this induced signature can be used to determine when re-stimulation may be needed in the oil producing system before the rate of oil production begins to decline for any given well. Additionally, as MEOR operations can alter the quality of the oil, changes in the oil quality pre- and post-stimulation can be monitored.

In addition to change in the hydrocarbon (e.g., methane) signatures, changes in the isotopic signatures of the biosurfactants, biopolymers, and organic acids that are produced as byproducts of the biogenic gas generation process can also be used to monitor stimulation operations. For example, the multiply substituted isotopologue signatures, clumped isotope signatures, and/or position-specific isotope signatures of the biosurfactants, biopolymers, and organic acids may change after a stimulation treatment due to being produced under nutrient oversupply conditions. As another example, due to changing environmental conditions (e.g., temperature, pressure, and/or salinity) in the reservoir or coalbed due to the stimulation operations, the indigenous microbial community may shift to favor certain microorganisms over other microorganisms. As the microbial community shifts to favor different dominant species, the various biosurfactants, biopolymers, and organic acids that are produced may change, and the isotopic signatures of the various biosurfactants, biopolymers, and organic acids that are produced may also shift. Similarly, if the stimulation operation involves the introduction of exogenous microorganism to the well, this may also cause changes in the isotopic signatures of the various biosurfactants, biopolymers, and organic acids that are produced as different microbial populations in the community are stimulated.

Isotopologue geochemistry is based on the variation in the distribution of isotopes within a molecule that give rise to molecules that are identical in their elemental composition, but that may differ in the isotopic composition of individual atoms within that molecule. These species are called isotopologues. For example, there are three isotopologues of nitrogen ($^{14}N_2$, $^{15}N$-$^{14}N$, and $^{15}N_2$). An isotopologue in which two or more rare isotopes are present is called a multiply substituted isotopologue, and an isotopologue in which two or more rare isotopes are in close proximity (i.e., isotopic "clumps") is called a clumped isotope (e.g., $^{15}N_2$). Hydrocarbon isotopologues involve hydrocarbon compounds (i.e., those that comprise carbon and hydrogen atoms) that have natural isotopes of $^{12}C$, $^{13}C$, $^{1}H$, or deuterium (D). Similarly isotopologues of biosurfactants (e.g., lipids), biopolymers, and organic acids can involve the natural isotopes of $^{12}C$, $^{13}C$, $^{1}H$, or deuterium (D). $^{12}C$ represents about 98.93 mole % of the total carbon on Earth, while $^{13}C$ forms the remaining 1.07 mole %. The isotopic abundance of $^{1}H$ on earth is 99.985 mole % while D has an abundance of 0.015 mole %. Thus, common volatile hydrocarbons can have large numbers of stable isotopologues (e.g., methane has 10, ethane has 36, and propane has 216). As an example, two common isotopologues of methane include $^{13}CH_3D$ or $^{12}CH_4$. Similarly, numerous stable isotopologues of different biosurfactants, biopolymers, and/or organic acids can exist.

In addition to the number of rare isotopes, the distribution of isotopes in the molecule can also provide information about the molecule. For example, in a linear hydrocarbon compound with three carbon atoms, the rare isotope can either take a central or terminal (end of the molecule) position. Similarly, rare isotopes of hydrogen can occupy different positions. As the size of the hydrocarbon or molecular compound increases, the number of positions that these rare isotopes can be situated increases. This effect is called the position specific isotope effect, or isotopomer geochemistry.

The multiply substituted isotopologue signature, clumped isotope signature, and/or position-specific isotope signature of any molecule is a function of (i) temperature-independent randomly populated processes (stochastic distribution) and (ii) other non-random mass fractionating processes. The stochastic distribution of any isotopologues can be determined from the bulk isotope signature of the species from which it derives. For example, determining the stochastic distribution of isotopologues for methane involves knowledge of the $^{13}C$ and D signatures of methane. At equilibrium, a non-stochastic distribution may result from thermodynamic differences between the different isotopologues. Under non-equilibrium conditions, the non-random processes may result be temperature-time dependent isotopic exchange reactions in the molecule.

Additional equilibrium or non-equilibrium kinetic isotope exchange processes may also influence the signatures in some molecules, such as hydrocarbons. These processes may include, but are not limited to, biodegradation, secondary thermal cracking of hydrocarbons, thermochemical oxidation/reduction, reactions, mixing, or diffusion. These process may differ in their relative magnitude of the impact on the multiply substituted isotopologue signatures, clumped isotope signatures, and/or position-specific isotope signatures. In addition to the size of the signatures, the time required for these processes to affect the signature may also differ from compound to compound. Integration of measured multiply substituted isotopologue signatures, clumped isotope signatures, and/or position-specific isotope signatures of multiple hydrocarbon species with an understanding of the kinetic properties of these species provides unique constraints on both the temperature at which the compounds is generated and/or stored in the subsurface. Kinetic properties of multiply substituted isotopologue signatures, clumped isotope signatures, and/or position-specific isotope signatures may be derived from laboratory experiments or modeling approaches as described in further detail below.

As an example, some hydrocarbon species may develop a signature that does not change over geologic timescales of billions of years if conditions or reactions change. One example of this is methane, which is believed to develop a multiply substituted isotopologue signature that is dominantly sensitive to temperature. This signature appears to develop during generation of the methane molecule and is then locked in even if the methane molecule is transported to a colder environment and stored. In contrast, other hydrocarbon molecules are sensitive to temperature may track changes in temperature over short timescales. For example, decane may initially develop a signature that records the temperature at which it was generated, but this signature may subsequently change to reflect increases or decreases in the temperature at which the compound resides over timescales of years. Another example may be that for some isotopologues, the isotope positions within molecules are sensitive to biodegradation and, if an understanding of the time taken to biodegrade the particular compound is possible one can determine how long the hydrocarbon has been undergoing biodegradation. Thus, by measuring the multiply substituted isotopologue signatures, clumped isotope signatures, and/or position-specific isotope signatures of multiple hydrocarbon compounds that are be sensitive to different parameters (e.g., temperature and/or pressure) and have different rates of reaction (i.e., different rates of exchange between the different isotopologues), different information about the history of the hydrocarbon may be determined following generation of the hydrocarbon.

The present techniques take advantage of isotopmer geochemistry and the rapid evolution of induced biogenic gases after microbial stimulation to distinguish "induced" gases and newly formed byproducts from those that existed pre-stimulation. Accordingly, the methods and techniques provide for methods and techniques to enhance reservoir surveillance or monitor the production of a well, and/or to provide a unique characterization of hydrocarbons and other byproducts that are produced before and after microbial stimulation. That is, the measurement of multiply substituted isotopologue signatures, clumped isotope signatures, and/or position-specific isotope signatures of the byproducts (such as hydrocarbons, biopolymers, biosurfactants, and organic acids) of microbial stimulation can provide an understanding of the generation of hydrocarbons, such as liquids or gases, from the stimulation process. Further, the measurement of multiply substituted isotopologue signatures, clumped isotope signatures, and/or position-specific isotope signatures can provide information about the generation, storage, and alteration of the produced hydrocarbons.

Therefore, the present methods and techniques involve measuring multiply substituted isotopologue signatures, clumped isotope signatures, and/or position-specific isotope signatures of one or more byproducts of microbial stimulation. For example, the methods may involve measuring and comparing pre- and post-stimulation isotopic signatures of hydrocarbon samples, such as methane, or of biosurfactants, biopolymers, and organic acids in the produced fluids, as further described with reference to FIG. 1.

Figure 1:
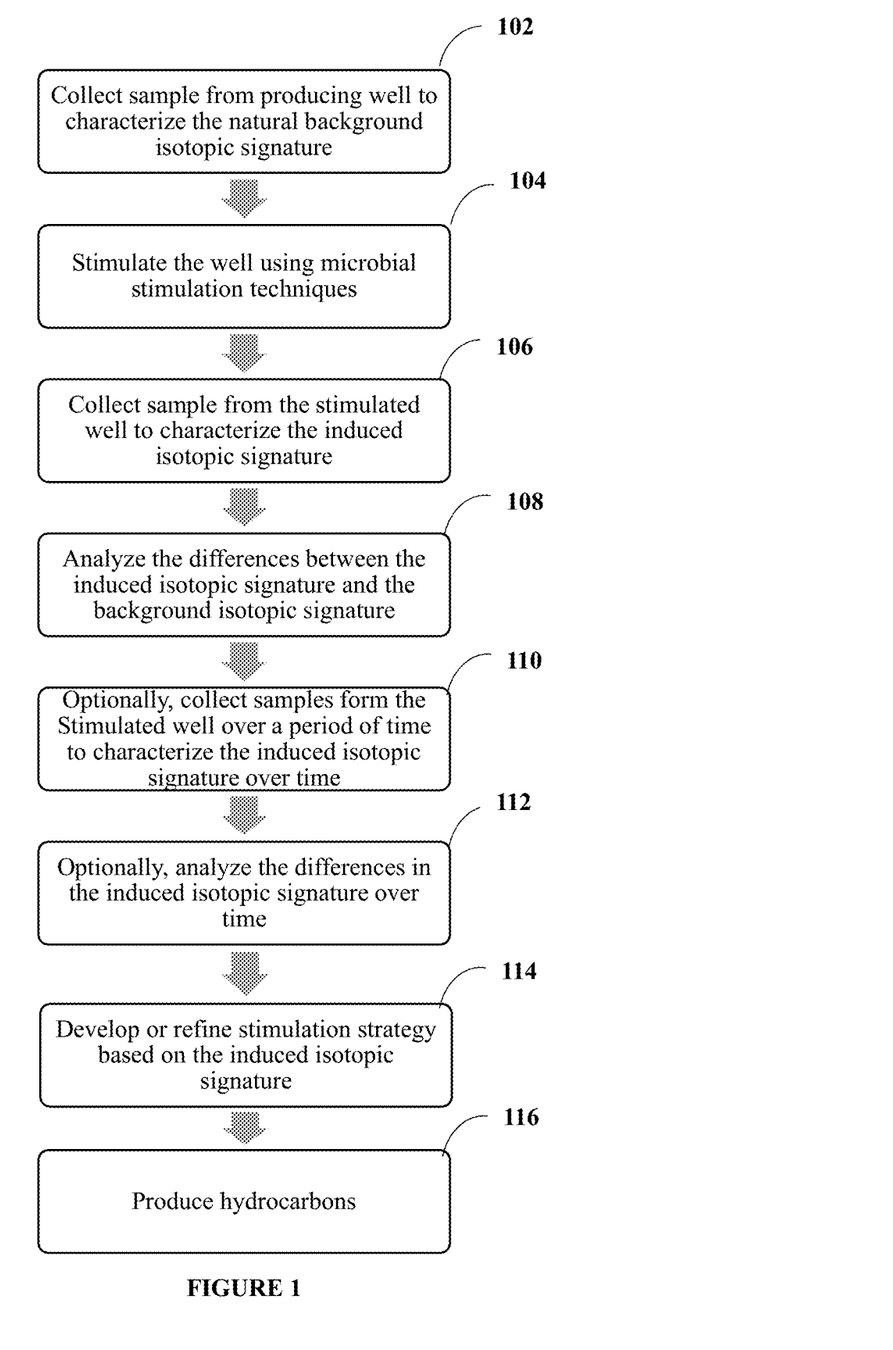
FIG. 1 is a flow diagram of an exemplary method of using isotopic signatures to monitor microbial stimulation of a well.

FIG. 1 is a flow diagram of an exemplary method to monitor the effects of a microbial stimulation on a production well, reservoir, or coalbed. This method may be used as part of a field deployable system, and/or as part of a reservoir surveillance program. The analysis based on such monitoring may be used to adjust or modify the microbial stimulation operations or hydrocarbon production operations.

At block 102 one or more samples from a subterranean formation are obtained. For example, the sample may be obtained from a wellbore, such as a wellbore of a producing or exploration well. The sample can be in the form of produced fluids, oil and/or gas obtained from the subsurface, and/or as a rock sample with hydrocarbons entrapped therein. The produced fluids may include hydrocarbons and other non-hydrocarbon fluids produced from the subsurface. The sample may also contain various biosurfactants, biopolymers, and organic acids. The samples are then analyzed for a geochemical signature, which includes a background isotopic signature. The background isotopic signature comprises one or more of a multiply substituted isotopologue signatures, clumped isotope signatures, and/or position-specific isotope signatures. This background isotopic signature can be used to develop a baseline isotopic signature for any background concentration of one or more of hydrocarbons, biosurfactants, biopolymers, and organic acids within the formation. In some preferred embodiments, the baseline isotopic signature includes an analysis of the relative proportion or concentration of the multiply substituted isotopologue $^{13}CH_3D$ as compared to other isotopes of methane in the sample.

The analysis of the hydrocarbon sample may involve determining the multiply substituted isotopologue signatures, clumped isotope signatures, and/or position-specific isotope signatures. The measurement of the absolute abundance of isotopologues or position of interest for any given hydrocarbon involves the knowledge of the molecular mass or absorption spectra at which they are present, and hence involves knowledge of the actual identity of each possible isotopologue for that species. Measurement of the abundance of each isotopologue or fragment can be conducted using multiple techniques, such as mass spectrometry or nuclear magnetic resonance.

As an example, one of the characteristics that impact the isotopologue signature of some hydrocarbons is the temperature of formation or storage. In particular, this temperature can be used to differentiate between different sources of hydrocarbons. This is done through first conversion of the multiply substituted isotopologue signatures, clumped isotope signatures, and/or position-specific isotope signatures to temperature (e.g., conversion of the concentration of the isotopologue in the sample to temperature). Temperature is an equilibrium signature that can be predicted by molecular modeling of equilibrium concentrations of multiply substituted isotopologue or positional effects, or may be determined empirically by measurements of signatures of a given hydrocarbon compound at different temperatures either in the presence or absence of a catalyst to accelerate equilibrium. Different hydrocarbon species have different rates of equilibration of their multiply substituted isotopologue signatures, clumped isotope signatures, and/or position-specific isotope signatures. For example, the $^{13}CH_3D$ isotopologue in methane may record methane generation temperature (see, e.g., Stolper et al., Science (2014)) and preserves the signature even when exposed to different temperatures during migration or uplift of the sediments in which the methane is contained.

However, if the signature is shown to be outside the range of an equilibrium signature, or appears to be unrelated to temperature, then other fractionating processes should be considered. These may include alteration processes, such as biodegradation, secondary cracking of hydrocarbons, or other processes, such as the results of a microbial stimulation as described herein.

The application of multiply substituted isotopologue signatures, clumped isotope signatures, and/or position-specific isotope signatures to determine temperatures involves the equilibrium relationship being known. This can be determined in several methods, which include experimental information, theoretical or computed information, and a combination of both. First, as in the above example regarding methane, laboratory experiments which measure the temperature and the compositions at equilibrium are both determined. The compositions are combined into approximate (ideal gas) equilibrium "constants" (they vary with temperature, but not pressure or composition), which can then be used along with bulk compositional information (D/H, $^{13}C/^{12}C$), to determine the equilibrium isotopic composition for any temperature or the temperature for any equilibrium composition. The distribution of isotopologues in a sample can be measured in the laboratory by any method or methods commonly used to measure composition, such as mass spectrometry, infrared and/or Raman spectroscopy, gas chromatography, nuclear magnetic resonance, etc. Isotopically labeled species can be used, increasing the overall amounts of rare isotopes so that the concentrations of naturally rare species can be measured more accurately.

Other than direct measurement of compositions, the equilibrium constants can be determined using properties of the individual isotopologues and the equations of statistical mechanics. See, e.g., D. MacQuarrie, Statistical Mechanics, University Science Books, pp. 113-159, (2000). The equations of statistical mechanics relate properties of the individual molecules (e.g., vibrational frequencies, moments of inertia, etc.) to partition functions (or partition function ratios) and the partition functions (or ratios) of a collection of molecules related via a chemical or isotopic transformation equation to the equilibrium constants. Of course there are various approximations available in statistical mechanics and different combinations of different properties of the molecules may be used to determine the partition functions or partition function ratios.

The most commonly used method uses experimentally measured vibrational frequencies from infrared and/or Raman spectroscopy and other molecular properties inferred from those spectroscopies. See e.g., Urey, H. C., et al., "Some Thermodynamic Properties of the $H^1H^2$, $H^2H^2$ Molecules and Compounds Containing the $H^2$ Atom", J. Chemical Physics, Vol. 1, pp. 137-143 (1933); Bigeleisen and Mayer, "Calculation of Equilibrium Constants for Isotopic Exchange Reactions", J. Chem. Phys., Vol. 15, No. 5, pp. 261-267, (1947); and Richet, Bottinga, and Javoy, "A Review Of Hydrogen, Carbon, Nitrogen, Oxygen, Sulphur, And Chlorine Stable Isotope Fractionation Among Gaseous Molecules", Annual Reviews In Earth and Planetary Sciences, Vol. 5, pp. 65-110 (1977). These methods use only the relatively few fundamental vibrational frequencies of the molecules, or the related harmonic frequencies (which are properties of the potential energy surface of the molecules and which are inferred from the experimental frequencies and other molecular properties). A related method, less dependent on approximations, uses substantially experimental information by directly summing partition function components from hundreds or thousands of vibrational/rotational spectroscopic lines. An example of such a method on the water molecule is provided by M. Vidler and J. Tennyson, "Accurate partition function and thermodynamic data for water", J. Chem. Phys., Vol. 113, No. 21, pp. 9766-9771 (2000).

For convenience and because of the difficulty of obtaining accurate experimental information on the various isotopologues of a given molecular species, modern quantum chemical calculations may also be used to provide the molecular properties, which are combined with statistical mechanical equations to yield partition functions, partition function ratios, and/or equilibrium constants. Often, similar or the same statistical mechanical equations are used as in the above methods, but the molecular properties and frequencies are calculated from quantum chemical methods. The most computationally efficient and commonly applied approach is to use the Urey or Bigeleisen-Mayer methods and to calculate "harmonic frequencies". These are frequencies, which are calculated from a harmonic oscillator (quadratic potential function) approximation of the interatomic potential energy surface of the molecules. Several points on the potential energy surface are calculated directly from quantum chemical methods. Potentially more accurate results for the partition functions and equilibrium constants can be generated using computed anharmonic frequencies (which correspond to measured fundamental frequencies) and other properties of the molecules and their potential energy surfaces. See, e.g., Liu et al., "On the proper use of the Bigeleisen-Mayer equation and corrections to it in the calculation of isotopic fractionation equilibrium constants", Geochimica et Cosmochimica Acta, Vol. 74, pp. 6965-6983 (2010). For some more complex molecules, physical and computational effects such as "resonance" are known to degrade the quality of the computed properties. These can partially be corrected using the methods discussed in Bloino et al., and as implemented in commercial quantum chemistry software. See e.g., J. Bloino, M. Biczysko, and V. Barone, "General Perturbative Approach for Spectroscopy, Thermodynamics, and Kinetics: Methodological Background and Benchmark Studies", J. Chem. Theory Comput., Vol. 8, pp. 1015-1036 (2012).

As an example, the methods of Bloino et al. may be used in the Gaussian 09 software (see, e.g., Gaussian 09, Revision D.01, Frisch et al., Gaussian, Inc., Wallingford Conn. (2009)) combined with the B3LYP density functional method or MP2 post-Hartree Fock ab initio method and the aug-cc-PVTZ basis set to compute anharmonic frequencies and other molecular constants for methane. These can be used with the simple perturbation theory of Truhlar et al. to provide partition functions and these combined to produce equilibrium constants. See, e.g., Truhlar, D. G. and Isaacson, A. D., "Simple perturbation theory estimates of equilibrium constants from force fields", J. Chem. Phys., Vol. 94 (1), pp. 357-359 (1991). Equations involving the equilibrium constants and the bulk isotopic signatures for $^{13}C$ and D can be solved using standard linear equation solvers in a package such as Matlab (see, e.g., MATLAB, The MathWorks, Inc., Natick, Mass., United States).

Other computational methods may be used to provide some or all of the information involved in predicting partition functions and equilibrium constants. For example, path integral Monte Carlo methods may be used. These have been applied to isotopic fractionation in methane and other molecules by Webb and Miller. See M. A. Webb and T. F. Miller, III, "Position-Specific and Clumped Stable Isotope Studies: Comparison of the Urey and Path-Integral Approaches for Carbon Dioxide, Nitrous Oxide, Methane, and Propane", J. Phys. Chem. A, Vol. 118, pp. 467-474 (2014). Ab initio Molecular Dynamics has been used to account for the influence of solvent fluctuations on isotopic fractionation by Rustad et al. See J. R. Rustad, E. J. Bylaska, V. E. Jackson, and D. A. Dixon, "Calculation of Boron-Isotope Fractionation Between $B(OH)_3(aq)$ and $B(OH)^-_4(aq)$", Geochimica et Cosmochimica Acta, Vol. 74, pp. 2843-2850 (2010).

Various options are available for the approximations and equations used from statistical mechanics. Similarly, there is a large variety of "model chemistries", which may be used to provide useful estimates of the molecular properties from computational quantum chemistry. The different methods may be distinguished by the use of ab initio theory or density functional theory. The methods may also be distinguished by different prescriptions for various physical and theoretical effects, such as electron exchange and correlation. The selection of a "basis set" to describe the possible states of electrons may be useful. Different methods and equations may be chosen for computing a harmonically-corrected molecular properties and for dealing with various forms of resonance interactions. The optimal combination of methods may depend on the accuracy desired, the software and computer hardware available, and the specific molecular systems of interest.

Position-specific isotope signatures are different than effects due to multiply substituted isotopologue signatures, but may be combined with other effects. The same theoretical and computational methods may be used to compute partition functions and equilibrium constants for position-specific isotopologues and their conversion reactions. Experimentally, some methods are not able to differentiate between position-specific isotopomers. For example, mass spectral methods that rely only on the parent molecular ion do not contain useful information on the position of the different isotopic atoms. However, fragments of the molecular ion may contain such information. The mass spectrum signals due to C2H5+ and CH3+ fragments of propane (and their 13C and D containing forms) are related to the relative amounts of the position specific forms of propane; e.g. (H3C)(CHD)(CH3) vs. (H3C)(CH2)(CH2D).

As an example, Wang et al. describes calculations of partition function ratios and fractionation factors for various positions in various functional groups for hydrocarbons and other organic molecules using density functional theory with the B3LYP functional and the 6-311G** basis set with further calibration to experiments on rapidly exchanging hydrogen positions adjacent to the carbonyl group in ketones. See, e.g., Y. Wang, A. L. Sessions, R. J. Nielsen, and W. A. Goddard, III, "Equilibrium 2H/1H fractionations in organic molecules: I. Experimental calibration of ab initio calculations", Geochimica et Cosmochimica Acta, Vol. 73, pp. 7060-7075 (2009).

Time-dependent behavior of multiply substituted isotopologues, clumped isotopes, and/or position-specific isotopes arise because not every natural process achieves equilibrium, even over geologic time-scales. Because chemical reaction rates generally decrease with temperature, for some processes, there exist "closure" or "blocking" temperatures. That is, closure or blocking temperatures are temperatures above which equilibrium is achieved on the time-scales of interest for a particular application, and below which equilibrium is not achieved on the time-scales of interest. For hydrocarbon systems analysis, if a sample which includes hydrocarbons and related molecular species, is cooled from some initially high temperature, the system may achieve equilibrium at a relatively high temperature, but this equilibrium may be 'frozen-in' at the blocking temperature and subsequent cooling does not re-set this equilibrium. The characteristic temperature determined from multiply substituted isotopologue signatures, clumped isotope signatures, and/or position-specific isotope signatures on a particular molecular type may then indicate this blocking temperature.

Methods used to determine the rates and temperature-dependence of isotope exchange reactions are related to those used to determine equilibrium. That is, the overall time-scale of interconversion as a function of temperature can provide useful information. The methods of measuring chemical rates is known in the art. One of the difficulties that has to be overcome in the experimental determination of rates as applied to geochemical processes is that those processes may effectively occur over geological time-scales, but not occur over laboratory time-scales. Sometimes increased temperatures are used to increase the rates into a measurable range and then an attempt is made to extrapolate the rates to the geological temperatures of interest. For example, the rates of hydrogen-isotope exchange reactions in hydrocarbons were investigated by Reeves et al. See, e.g., E. P. Reeves, J. S. Seewald, S. P. Sylva, "Hydrogen isotope exchange between n-alkanes and water under hydrothermal conditions", Geochimica et Cosmochimica Acta, Vol. 77, pp. 582-599 (2012). This extrapolation may be inaccurate and, in addition, the relative rates of different processes may be different at different temperatures. For these reasons and others, the theoretical and/or computational approaches may be used to determine estimates of rates.

Methods of computing estimates of rates are also well known in the art. See, e.g., Transition State Theory, S. Glasstone, K. J. Laidler, and H. Eyring, "The Theory of Rate Processes", McGraw-Hill, New York (1941). The estimates may be less accurate than those of isotopic equilibrium phenomena (e.g., may only be accurate to within an order of magnitude), but the estimates may be useful for establishing approximations to blocking temperatures. Many of the same choices of methods and parameters that are be made in computing equilibrium properties are necessary in computing rates via computational chemistry methods.

Temperature is an equilibrium signature that can be predicted by molecular modeling of equilibrium concentrations of multiply substituted isotopologue or positional effects, or may be determined empirically by measurements of signatures of a given hydrocarbon compound at different temperatures either in the presence or absence of a catalyst to accelerate equilibrium. Different hydrocarbon species have different rates of equilibration in multiply substituted isotopologues. For example, methane records methane generation temperature and preserves this signature even when exposed to different temperatures. In contrast, a molecule such as decane may give a temperature that reflects the temperature at which it has been stored over the past several years because it can undergo intra-molecular isotope exchange over faster timescales than methane. Historical temperatures obtained from the clumped or position specific isotope signatures may be different for different species because each of these hydrocarbon compounds record different parts of the history of the bulk hydrocarbon given their different kinetic behaviors.

The kinetic properties for different hydrocarbon compounds can be determined through different approaches. One approach may be to determine kinetic parameters experimentally. This can be done, for example, by subjecting any hydrocarbon compound to a range of temperatures with or without the presence of a catalyst for different periods of time. See, e.g., Stolper, D. A. et al., (2014), "Formation temperatures of thermogenic and biogenic methane", Science, Vol. 344, pp. 1500-1503. The hydrocarbon compounds taken from these different experiments are analyzed and its kinetic properties can be determined for any given temperature based on how quickly equilibration is reached at different temperatures in each experiment.

An alternative approach may be to use molecular modeling to predict the timescales at which the multiply substituted isotopologue signature and/or position specific isotope signature of any given hydrocarbon compound.

Based on data from either of these different approaches, a model can be developed to provide kinetic parameters for any hydrocarbon compound. From this model, a present day signature can be corrected for any historical change in its signature based on changes in temperature over some period of time to determine the signature, and from this a historical temperature, for any hydrocarbon compound for any time of interest.

Thus, using the above described methods one can determine the background isotopic signature of the sample, that utilizes one or more of multiply substituted isotopologue signatures, clumped isotope signatures, and/or position-specific isotope signatures. The background isotopic signature may be used to determine the temperature at which the hydrocarbons in the sample were generated or altered, which can also be used to give an indication of the age of the hydrocarbons in the sample.

Returning to FIG. 1, at block 104 microbial stimulation techniques are used to stimulate the reservoir. Any known microbial stimulation technique may be used. Preferably the microbial stimulation technique comprises introducing various reactants and/or nutrients into the subterranean formation, introducing exogenous microbial populations into the subterranean formation, and combinations thereof.

In some embodiments, the microbial stimulation techniques may involve the introduction of various reactants and nutrients into the subterranean formation. Any nutrients, reactants, and additives as known in the art may be used. The nutrients may be chosen to be those that are selectively desired by one or more of the microorganisms already present in the subterranean formation. That is, the nutrients may be chosen to promote the growth of one or more of the indigenous species (or one or more of the exogenous species being injected) over other indigenous species currently in the formation. This can allow for selective promotion of the microorganism that have desirable properties over others.

In some embodiments, the microbial stimulation techniques may involve the injection of an exogenous microbial population into the subterranean formation. For example, an inoculating culture may be supplied with various nutrients and additives to water or other fluids being pumped into a well in the formation. Any suitable microorganism may be used. However, care should be taken to choose a microorganism that can survive in the conditions that prevail in the formation. That is, microorganisms should be chosen that can thrive in the formation despite any physical constraints, such as small and variable formation pore sizes, and environmental constraints, such as high temperature, high salinity, high pressure, and lack of oxygen, that are found in the formation. Other biological constraints, such as competition from indigenous microbes and the stress of changing environments (e.g., moving from surface to subsurface) may also limit the viability of exogenous microorganisms. Various different microorganisms and combinations of microorganism as known in the art may be used. Useful microorganisms may include, but not be limited to, microorganisms from the genera of *Clostridium, Bacillus, Pseudomonas, Xanthomonas, Leuconostoc, Desulfovibro, Athrobacter, Corynebacterium, Enterobacter*, and combinations thereof. Useful microorganism may also include, but not be limited to, those selected from the following species: *Bacillus lichenifornis; Leuconostoc mesenteroides; Xanthomonas campestris; Acinetobacter calcoaceticus; Arthrobacter paraffineus; Bacillus licheniformis; Clostridium pasteurianum; Corynebacterium fasciens; Pseudonomas rubescens; Bacillus polymyxa; Brevibacterium viscogenes; Clostridum acetobutylicum; Zymomonas mobilis; Enterobacter aerogenes; Clostrodium acetobutylicum; Enterobacter aerogenes*; and combinations thereof.

The exogenous microbial populations may also be chosen to effect certain properties of the hydrocarbon recovery. For example, when seeking to decrease the interfacial tension or reduce the viscosity of the hydrocarbons in the formation, microorganisms that are known to be good producers of biosurfactants may be chosen. For example, *Acinetobacter calcoaceticus; Arthrobacter paraffineus; Bacillus licheniformis; Clostridium pasteurianum; Corynebacterium fasciens; Pseudomonas rubescens*, and combinations thereof may be used. Alternatively, when seeking to increase the permeability of the formation and improve the emulsification of the hydrocarbons, microorganisms that produce organic acids (e.g., acetate, butyrate) as by-products may be desired. For example, various species of *Clostridum* may be used, or *Enterobacter aerogenes*.

At block 106 a sample is taken after the stimulation. The post-stimulation sample is analyzed for the induced isotopic signature. The methods described above that are used to determine the background isotopic signature can be used to determine the induced isotopic signature. Then, at block 108 the induced isotopic signature is compared to the baseline or background isotopic signature.

The time interval between sample acquisition, measurement, and analysis can have numerous valuable reservoir surveillance and well monitoring applications. For example, daily logs of induced isotope signatures collected during the stimulation operations can be utilized to provide information on the efficiency of the stimulation techniques. An example of this could be that over time the effect from the stimulation may decrease and thus the induced isotopic signature will begin to converge back to the baseline isotopic signature over time. If this occurs, the production operation may be adjusted to perform another microbial stimulation. Another example may include monitoring of real-time or concurrent multiply substituted isotopologue, clumped isotope, and/or position-specific isotope data from analysis of co-mingled hydrocarbons in a production stream to identify changes in the hydrocarbon signature that is associated with the stimulation operations. This information could suggest that the pressure is being drawn down in one region and has resulted in a decreased contribution. Similarly, this information could suggest that the nutrient supply is decreasing and has resulted in the microbial community reverting back to the baseline production. This information could then be used to change the stimulation strategy (e.g. increase the addition of certain nutrients over others) to ensure long term fluid production and maximize the lifespan of the well. These measurements therefore provide a more cost effective and rapid methodology, and allow for early identification of the performance of the stimulation operations that current monitoring methodologies do not allow.

In some embodiments, the induced isotopic signature may be converted in a temperature, for example using the methods described above for converting the baseline isotopic signature into a temperature. However, where the temperature of the baseline isotopic signature can indicate the formation or generation temperature of the hydrocarbons, the temperature of the induced isotopic signature is likely not at equilibrium as it was produced under oversupply of nutrient conditions in shorter time scales. Thus, a comparison of the temperatures of the pre- and post-stimulation samples can give an indication of how effective the stimulation techniques are. That is, if the post-stimulation samples exhibit an isotopic signature and formation temperature that are similar to the pre-stimulation samples, one can tell that the stimulation techniques have not been effective.

Figure 2:
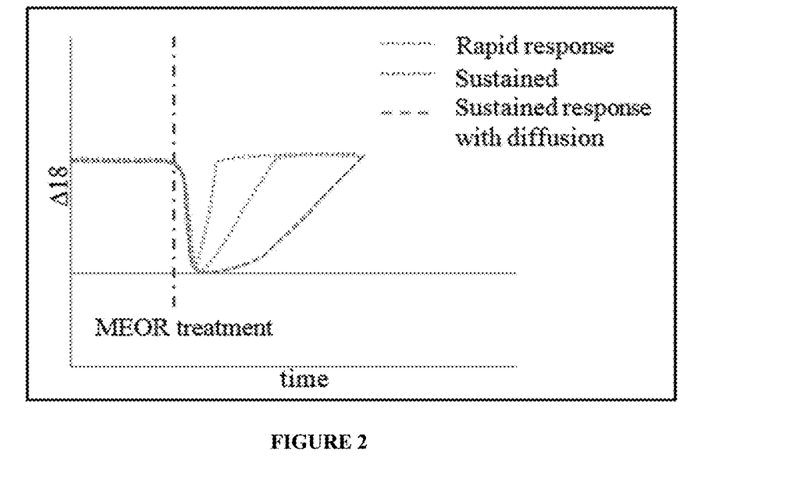
FIGS. 2 and 3 are exemplary isotopic signatures that can be utilized for determining the effectiveness of a microbial stimulation.

The induced isotopic signature can provide information about how effective the stimulation techniques have been. For example, in FIG. 2 an increase in thermogenic hydrocarbon signatures (the rapid response) can indicate that the stimulation technique has been effective at releasing trapped thermogenic hydrocarbons that had been trapped in pores or sorbed to the organic matrix in the formation. This can be compared with the increase in production of the biogenic hydrocarbon signatures (the sustained response) which can indicate that the stimulation technique has been effective at creating new biogenic hydrocarbons and releasing any previously trapped biogenic hydrocarbons. By examining the multiply substituted isotopologue signatures, clumped isotope signatures, and/or position-specific isotope signatures of the biogenic gas signatures, one can further tell if they are newly created biogenic gases from the stimulation techniques or if they are pre-stimulation biogenic gases.

Figure 3:
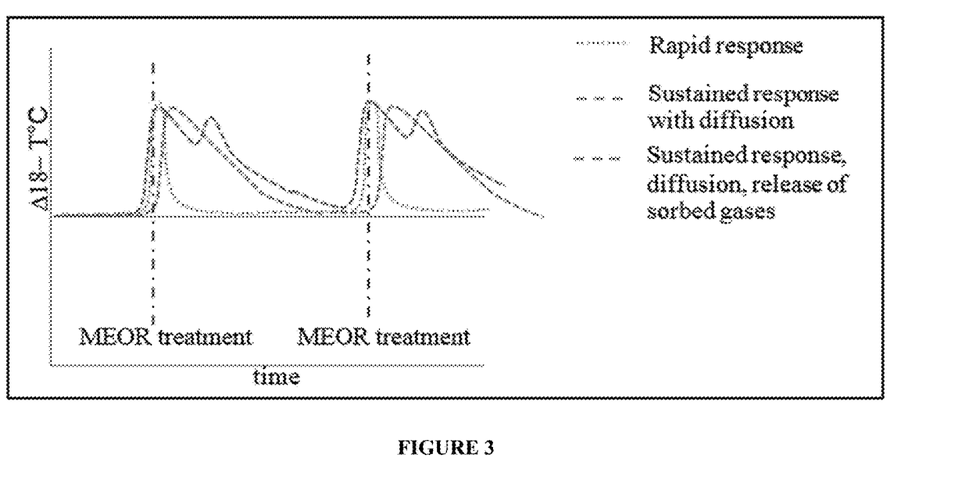

FIG. 3 provides an example of a schematic for prediction a rapid response shift in the inferred temperatures due to increased induced biogenic gas production, a shift in inferred temperatures with a gradual return to background temperatures (the sustained response), and rapid shift in inferred temperatures with a gradual return followed by an increase associated with additional thermogenic gas release. Also as illustrated in FIG. 3, as the shifts in the isotopic signatures return the baseline levels this can indicate that a re-stimulation techniques is needed.

Returning to FIG. 1, at block 110, one or more additional samples are optionally obtained at later times. These additional samples can be analyzed to determine how the induced isotopic signature changes over time. For example, the additional samples may be obtained at specific time intervals, such as every hour, or every 1 to 3 hours, or every 5 to 24 hours, or every 24 to 72 hours, or weekly. As described above, using multiple samples can create a log of the isotopic responses from the microbial stimulation that can be used to evaluate the effectiveness of the stimulation techniques.

At block 114, the production or stimulation strategy may be refined or modified. For example, the results of the comparisons made at blocks 108 and/or 112 may be used to support decisions regarding whether re-stimulation is needed, or whether the stimulation strategy needs to be modified. For example, if after multiple stimulation procedures the spikes in the thermogenic hydrocarbon responses are decreasing, this can indicate that the vast majority of the trapped hydrocarbons have been released. As such, any new stimulation techniques may want to focus on the creation of new biogenic gases. Alternatively, if after a stimulation procedure the isotopic responses indicate that there is only an increase in biogenic gas production, a new stimulation procured may be contemplated that would instead enhance the release of trapped thermogenic hydrocarbons.

At block 116 the strategies may then be used to produce hydrocarbons. Producing hydrocarbon may include operations such as hydrocarbon extraction, along with injection of gas or liquid for increasing drive pressure, mobilizing the hydrocarbon or treating by, for example chemicals or hydraulic fracturing the wellbore to promote increased flow, well servicing, well logging, and other well and wellbore treatments.

As an example scenario, the present methods and techniques may be used with MECoM stimulation of coalbeds. For example, a field that is producing coalbed methane may begin to experience declines in the rate of methane production at producing wells. Prior to stimulation, the methane sampled at a producing well has an equilibrium methane clumped isotope signature for primary biogenic gas. This equilibrium signature can be used to determine that the biogenic gas has a generation temperature of less than 80° C. MECoM is performed to stimulate the in-situ microbial communities in the coalbed to generate more methane by further biodegradation of the coal. Upon generation of the induced methane, the induced methane mixes with the residual primary, inherited methane. Samples are taken from the well over a period of time to identify when this induced methane arrives at the well bore, and how much induced methane is produced relative to the original primary methane. The bulk carbon isotopes signature of the gases may not shift sufficiently with MECoM treatments to resolve the induced vs. inhereited biogenic gas, so long as the microbial community and/or metabolic pathways are relatively similar pre- and post-treatment. In this scenario, as the in-situ microbial community is stimulated, it is likely that the metabolic pathways pre- and post-treatment will be similar, and thus, that the bulk isotopic composition of the methane will be similar for both sources of gas. However, in contrast, the relative concentrations of the clumped isotopes, multiply substituted isotopologues, and/or position specific isotopologues of the methane will change after treatment because the microbial processes were driven to excess post-treatment by excess reactants and nutrients. This produces a large KIE in the induced methane. Therefore, analysis of methane sampled from the well post-treatment can be used to quantify how much induced methane is present in the gas mixture. This approach can also be used to test different mixes of nutrient supplies in the stimulating fluid to see which mixes generate the largest gas induced volumes. This approach can also be used to identify the period of time over which the induced methane continues to be produce. By doing this, the operator can develop the most effective nutrient supply and program of stimulation frequency to optimize the generation and production of coalbed methane.

As another example scenario, the present methods and techniques may be used to improve recovery of oil in a producing field using MEOR. For example, as the volume of oil being produced from a well in an oil field starts to decline and the total volume produced since the field began is approaching the estimated ultimate recovery factor for the field, the well can be sampled to characterize the natural background signature of the subsurface hydrocarbons. MEOR is performed to stimulate a subsurface microbial community that can access and mobilize currently unproducible oil in the subsurface. The MEOR process produces induced biogenic methane as a by-product, and may also alter the organic acids and biosurfactants in the well's produced fluids. The induced biogenic methane mixes with the indigenous thermogenic hydrocarbons. The bulk isotopic signature may be used to distinguish the thermogenic hydrocarbons from the biogenic hydrocarbons. However, by analyzing the differing clumped isotope signatures, multiply substituted isotopologue signatures, and/or position specific isotopologue signatures, one may be able to compare the efficiency and effectiveness of different simulations recipes over time. Larger deviations may suggest that more induced gas is generated. This may also correspond to larger volumes of oil accessed and produced, thereby increasing the recovery factor of the field. When the induced isotopic signature deviation in the produced fluids begins to decrease, the field can be re-stimulated.

As described herein, the quantification of clumped isotopes, multiply substituted isotopes, and/or position specific isotope signatures of hydrocarbons can be used as part of a reservoir surveillance or well monitoring program. The signatures can provide diagnostic information regarding the history of the hydrocarbons and therefore provide information regarding source, alteration, etc.

The methods and techniques described herein may utilize a computer system. For example, the computer system may comprise a central processing unit (CPU) that is coupled to system bus. The CPU may be any general-purpose CPU, although other types of architectures of CPU may be used as long as CPU supports the inventive operations as described herein. The CPU may execute the various logical instructions according to various exemplary embodiments. For example, the CPU may execute machine-level instructions for performing processing according to the operational flow described above.

The computer system may also include computer components such as a random access memory (RAM), which may be SRAM, DRAM, SDRAM, or the like. The computer system may also include read-only memory (ROM), which may be PROM, EPROM, EEPROM, or the like. RAM and ROM hold user and system data and programs, as is known in the art. The computer system may also include an input/output (I/O) adapter, GPU(s), a communications adapter, a user interface adapter, and a display adapter. The I/O adapter, the user interface adapter, and/or communications adapter may, in certain embodiments, enable a user to interact with computer system in order to input information.

The I/O adapter preferably connects a storage device(s), such as one or more of hard drive, compact disc (CD) drive, floppy disk drive, tape drive, etc. to computer system. The storage device(s) may be used when RAM is insufficient for the memory requirements associated with storing data for operations of embodiments of the present techniques. The data storage of the computer system may be used for storing information and/or other data used or generated as disclosed herein. The communications adapter may couple the computer system to a network (not shown), which may enable information to be input to and/or output from system via a network (for example, the Internet or other wide-area network, a local-area network, a public or private switched telephony network, a wireless network, any combination of the foregoing). A user interface adapter couples user input devices, such as a keyboard, a pointing device, and the like, to computer system. The display adapter is driven by the CPU to control, through a display driver, the display on a display device. Information and/or representations pertaining to a portion of a supply chain design or a shipping simulation, such as displaying data corresponding to a physical or financial property of interest, may thereby be displayed, according to certain exemplary embodiments.

The architecture of system may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to the embodiments.

As an example, machine-readable logic or code may be used or executed with a computing system. The code or a set of instructions is provided enhancing hydrocarbon production operations, which may include analyzing hydrocarbon samples for geochemical signature comprising clumped isotope signature, multiply substituted isotope signature, and/or position specific isotope signatures. When executed or applied with a computer system, such as computer system, code or set of instructions is configured to: analyze one or more of hydrocarbon samples from the subsurface formation for a baseline geochemical signature, wherein the baseline geochemical signature is based on clumped isotope signature, multiply substituted isotopologue signature, and/or position specific isotope signature; analyze one or more hydrocarbon samples obtained from the subsurface location at a time after a microbial stimulation operation for a induced geochemical signature, wherein the induced geochemical signature is based on clumped isotope signature, multiply substituted isotopologue signature, and/or position specific isotope signature; and compare the induced geochemical signature with the baseline geochemical signature.

In addition, the set of instructions may be configured to provide other enhancements. For example, the set of instructions may be further configured to: adjust a production or stimulation strategy based on the comparison. Also, the set of instructions may be further configured to: convert each baseline geochemical signature into a baseline temperature; and convert the induced geochemical signatures into an induced temperature; and compare the induced temperature with the baseline temperature. Further, the set of instructions may be further configured to: identify a source contribution for the induced geochemical signature based on the baseline geochemical signature.

In addition, the set of instructions may be further configured to: detect of elevated or decreased hydrocarbon presence; and transmit a notification to a field deployable system to obtain a sample from the subsurface location to analyze for an induced geochemical signature. The set of instructions may be further configured to: monitor for changes in the produced fluids of organic acids and biosurfactants; and/or monitor for stable isotope geochemistry changes in the produced fluid in one or more of organic acids and biosurfactants.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention has been described above with reference to numerous embodiments and specific examples. Many variations will suggest themselves to those skilled in this art in light of the above detailed description. All such obvious variations are within the full intended scope of the appended claims.

The invention claimed is:

1. A method of producing hydrocarbons comprising:
    (a) obtaining one or more samples from a well in a region of interest;
    (b) analyzing the one or more samples to determine a baseline isotopic signature, wherein the baseline isotopic signature comprises one or more of multiply substituted isotopologue signatures, clumped isotope signatures, and position-specific isotope signatures;
    (c) performing a microbial stimulation operation on the region of interest;
    (d) obtaining one or more post-stimulation samples from the well;
    (e) analyzing the post-stimulation sample to determine an induced isotopic signature, wherein the induced isotopic signature comprises multiply substituted isotopologue signatures, clumped isotope signatures, and/or position-specific isotope signatures;
    (f) comparing the baseline isotopic signature and the induced isotopic signature;
    (g) using the comparison to determine whether the type of hydrocarbons being produced from the well has changed, wherein the type of hydrocarbons being produced from the well comprises thermogenic hydrocarbons, biogenic hydrocarbons, and induced biogenic hydrocarbons; and
    (h) updating or refining the microbial stimulation operation based on the type of hydrocarbons being produced from the well.

2. The method of claim 1, wherein the sample comprises produced fluids from the well.

3. The method of claim 1, wherein the sample comprises hydrocarbons.

4. The method of claim 1, wherein the sample comprises one or more of biosurfactants, biopolymers, and organic acids.

5. The method of claim 1, wherein the microbial stimulation operation comprises introducing nutrients into the region of interest.

6. The method of claim 5, wherein the nutrients comprise one or more of molasses, nitrates, vitamins, and surfactants.

7. The method of claim 1, wherein the microbial stimulation operation comprises introducing an exogenous microbial population to the region of interest.

8. The method of claim 7, wherein the exogenous microbial population is introduced to the region of interest by injection of a solution comprising the exogenous microbial population in the well.

9. The method of claim 1, wherein the comparison of the baseline isotopic signature and the induced isotopic signature comprises a comparison of the change in the $^{13}CH_3D$ concentration.

10. The method of claim 1, wherein the comparison of the baseline isotopic signature and the induced isotopic signature comprises a comparison of the change in the $^{12}CH_2D_2$ concentration.

11. The method of claim 1, wherein the multiply substituted isotopologue signature, clumped isotope signature, or position-specific isotope signature is determined by:
- modeling an expected temperature-concentration dependence of the isotopologues for a hydrocarbon species of interest;
- measuring the concentration of isotopologues of the hydrocarbon species of interest present in the sample;
- comparing the measured concentration of isotopologues with the expected concentration of isotopologues; and
- converting the measured concentration of isotopologues to a storage temperature of the hydrocarbon species of interest.

12. The method of claim 1, further comprising developing a new stimulation strategy based on the type of hydrocarbons being produced in the well.

13. The method of claim 1, further comprising producing hydrocarbons.

14. A method of producing hydrocarbons comprising:
- (a) obtaining one or more hydrocarbon samples from a well in a region of interest;
- (b) analyzing the one or more samples to determine a baseline isotopic signature for a hydrocarbon species of interest, wherein the baseline isotopic signature comprises one or more of multiply substituted isotopologue signatures, clumped isotope signatures, and position-specific isotope signatures;
- (c) performing a microbial stimulation operation on the region of interest, wherein the microbial stimulation operation comprises at least one of introducing nutrients into the region of interest or introducing an exogenous microbial population to the region of interest;
- (d) obtaining one or more post-stimulation hydrocarbon samples from the well;
- (e) analyzing the post-stimulation sample to determine an induced isotopic signature for the hydrocarbon species of interest, wherein the induced isotopic signature comprises multiply substituted isotopologue signatures, clumped isotope signatures, and/or position-specific isotope signatures;
- (f) comparing the baseline isotopic signature and the induced isotopic signature to determine whether the type of hydrocarbons being produced from the well has changed, wherein the type of hydrocarbons being produced from the well comprises thermogenic hydrocarbons, biogenic hydrocarbons, and induced biogenic hydrocarbons; and
- (g) modifying the microbial stimulation operation by at least one of changing the type of nutrients being introduced to the region of interest, changing the volume or rate of nutrients being introduced to the region of interest, and changing the community composition of the exogenous microbial population being introduced to the region of interest; wherein the modifying is based on the comparison of the baseline isotopic signature and the induced isotopic signature.

15. The method of claim 14, wherein the nutrients comprise one or more of molasses, nitrates, vitamins, and surfactants.

16. The method of claim 14, wherein the comparison of the baseline isotopic signature and the induced isotopic signature comprises a comparison of the change in the $^{13}CH_3D$ concentration.

17. The method of claim 14, wherein the comparison of the baseline isotopic signature and the induced isotopic signature comprises a comparison of the change in the $^{12}CH_2D_2$ concentration.

18. The method of claim 14, further comprising producing hydrocarbons.

* * * * *